(12) United States Patent
Vange et al.

(10) Patent No.: US 11,685,708 B2
(45) Date of Patent: Jun. 27, 2023

(54) ACRYLAMIDE PHOTOINITIATORS

(71) Applicant: Coloplast A/S, Humlebaek (DK)

(72) Inventors: Jakob Vange, Helsingoer (DK); Petr Sehnal, York (GB); David Jepson, Harrogate (GB); Andrew Towns, Leeds (GB)

(73) Assignee: Coloplast A/S, Humlebaek (DK)

( * ) Notice: Subject to any disclaimer, the term of this patent is extended or adjusted under 35 U.S.C. 154(b) by 265 days.

(21) Appl. No.: 17/031,907

(22) Filed: Sep. 25, 2020

(65) Prior Publication Data

US 2021/0171438 A1 Jun. 10, 2021

Related U.S. Application Data

(63) Continuation of application No. 16/494,778, filed as application No. PCT/DK2018/050053 on Mar. 22, 2018, now Pat. No. 10,851,045.

(30) Foreign Application Priority Data

Mar. 31, 2017 (DK) ............................ PA 2017 70237

(51) Int. Cl.
  *C07C 231/06* (2006.01)
  *C07C 233/33* (2006.01)
  *C07C 233/51* (2006.01)

(52) U.S. Cl.
  CPC .......... *C07C 231/06* (2013.01); *C07C 233/33* (2013.01); *C07C 233/51* (2013.01)

(58) Field of Classification Search
  CPC .... C07C 231/06; C07C 233/33; C07C 233/51
  See application file for complete search history.

(56) References Cited

U.S. PATENT DOCUMENTS

| 5,202,483 | A | * | 4/1993 | Rehmer | ................ | C07C 233/31 |
|---|---|---|---|---|---|---|
| | | | | | | 562/451 |
| 5,506,279 | A | ‡ | 4/1996 | Babu | .................... | C07C 233/49 |
| | | | | | | 522/34 |
| 6,011,077 | A | ‡ | 1/2000 | Muller | ..................... | C08F 8/00 |
| | | | | | | 522/35 |
| 6,245,922 | B1 | ‡ | 6/2001 | Heilmann | ................ | C08F 2/48 |
| | | | | | | 552/20 |
| 6,673,850 | B1 | ‡ | 1/2004 | Yamato | ............... | C08F 293/005 |
| | | | | | | 522/33 |
| 8,414,982 | B2 | ‡ | 4/2013 | Hayoz | ...................... | C07F 9/54 |
| | | | | | | 427/51 |
| 10,851,045 | B2 | * | 12/2020 | Vange | .................. | C07C 231/06 |
| 2008/0021126 | A1 | ‡ | 1/2008 | Dietliker | ................ | G03F 7/031 |
| | | | | | | 522/34 |
| 2009/0098359 | A1 | ‡ | 4/2009 | Waller, Jr. | ................ | B32B 5/24 |
| | | | | | | 428/30 |
| 2010/0137469 | A1 | ‡ | 6/2010 | Zhu | ...................... | C07D 203/10 |
| | | | | | | 522/33 |

FOREIGN PATENT DOCUMENTS

| CN | 101225142 A | ‡ | 7/2008 | |
|---|---|---|---|---|
| CN | 103951576 A | ‡ | 7/2014 | |
| EP | 0456040 A1 | ‡ | 11/1991 | ......... C07D 295/185 |
| EP | 2353736 A1 | ‡ | 8/2011 | .............. B05D 1/42 |
| JP | 4038600 A | ‡ | 2/1992 | |
| JP | 10330317 A | ‡ | 12/1998 | |
| WO | WO-9510552 A1 | ‡ | 4/1995 | ......... C07C 237/22 |
| WO | WO-9624077 A1 | ‡ | 8/1996 | ............... C08F 8/30 |
| WO | WO-9705101 A1 | ‡ | 2/1997 | ......... C07C 233/49 |
| WO | WO-0220625 A1 | ‡ | 3/2002 | ............... C08F 8/30 |
| WO | WO-09048933 A1 | ‡ | 4/2009 | |
| WO | WO-09146321 A1 | ‡ | 12/2009 | |
| WO | WO-09148869 A1 | ‡ | 12/2009 | |
| WO | WO-10033794 A1 | ‡ | 3/2010 | |
| WO | WO-10033807 A1 | ‡ | 3/2010 | |
| WO | WO-10065355 A1 | ‡ | 6/2010 | |
| WO | WO-11152967 A2 | ‡ | 12/2011 | |
| WO | WO-11153085 A2 | ‡ | 12/2011 | |
| WO | WO-12134636 A1 | ‡ | 10/2012 | |
| WO | WO-14052215 A1 | ‡ | 4/2014 | |
| WO | WO-15167819 A1 | ‡ | 11/2015 | |

OTHER PUBLICATIONS

Ninomiya et al. "A New Synthesis of Benzo[a]quinolizines Related to Ipecac Alkaloids", Heterocycles Communication Special Issue, vol. 6, No. 11, Jan. 1, 1977, pp. 1799-1803.‡
Roberts et al. "Chemoproteomic Screening of Covalent Ligands Reveals UBA5 As a Novel Pancreatic Cancer Target", ACS Chemical Biology, vol. 12, No. 4, Feb. 15, 2017, pp. 899-904.‡
"RN: 1129603-79-7", STN on the Web REGISTRY Database, Chemical Abstract RN, 2009, pp. RN: 1129603-79-7.
Parris Cheser L., "N-Benzylacrylamide", Organic syntheses, 1962, pp. 16-18, vol. 42.

* cited by examiner
‡ imported from a related application

*Primary Examiner* — Yong L Chu
(74) *Attorney, Agent, or Firm* — Coloplast Corp., Coloplast A/S; Nick Baumann

(57) ABSTRACT

Acrylamide photoinitiators are provided, in which a photoinitiator moiety and an acrylamide are incorporated into the photoinitiator structure.

1 Claim, No Drawings

ACRYLAMIDE PHOTOINITIATORS

SUMMARY

The present invention relates to photoinitiators with an acrylamide functionality. The photoinitiators can be readily synthesised and are stable in acidic environments.

BACKGROUND

Curing via ultraviolet (UV) radiation requires efficient methods of initiating the chemical reaction responsible for the curing process. Photoinitiators convert radiation into chemical energy, and are employed in many cases to promote curing of various materials.

Despite previous efforts, there remains a need for novel photoinitiators which can be easily synthesised and which are chemically stable, especially in acidic environments.

SUMMARY

A photoinitiator of the general formula (I) is thus provided:

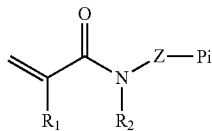

in which $R^1$, $R^2$ and Z are as defined herein, and in which Pi is a photoinitiator, preferably a Norrish type-I photoinitiator moiety.

Photoinitiators having the general formula (I) avoid potentially acid-sensitive groups, in particular esters in the Z-linker.

A method for synthesising the photoinitiators of the general formula (I) is also provided.

Further aspects are presented in the following description and dependent claims.

DETAILED DISCLOSURE

Definitions

In the following, when a part of a molecule is described as "optionally substituted" it is meant that said part may be substituted by one or more substituents selected from: $C_1$-$C_6$ linear, branched or cyclic alkyl, aryl, —OH, —CN, halogens, amines, amides, alcohols, ethers, thioethers, sulfones and derivatives thereof, sulfoxides and derivatives thereof, carbonates, isocyanates, nitrates and acrylates. Notably, when Z is $C_1$-$C_{12}$ alkylene substituted with a $C_1$-$C_6$ alkyl substituent, said $C_1$-$C_6$ alkyl substituent may form one or more rings with the photoinitiator moiety Pi.

The term "heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. Preferred heterocyclyls contain about 5 to about 6 ring atoms. The prefix aza, oxa or thia before the heterocyclyl root name means that at least a nitrogen, oxygen or sulfur atom respectively is present as a ring atom. The heterocyclyl can be optionally substituted as described above. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like.

The term "alkylene" is used in the following to specify moieties derived from alkanes in which two H atoms have been removed to form a diradical species. The simplest alkylene is methylene —$CH_2$—, and other alkylenes include ethylene —$CH_2$—$CH_2$—, propylene —$C_3H_6$— and butylene —$C_4H_8$—. The term "alkylene" includes branched, linear and cyclic alkylenes, with branched alkylenes being most preferred. An alkylene which is a $C_1$-$C_{12}$ alkylene is one which contains between 1 and 12 carbon atoms. Preferred alkylenes contain between 1 and 6 carbon atoms (i.e. $C_1$-$C_6$ alkylenes).

The term "alkenylene" is used in the following to specify moieties derived from alkenes in which two H atoms have been removed to form a diradical species. Examples include ethyenylene —$CH_2$=$CH_2$— and propenylene —$C_3H_4$— moieties. The term "alkenylene" includes branched, linear and cyclic alkenylene, with linear alkenylene being most preferred.

The terms "aryl" or "arylene" are used to define an unsaturated cyclic system which contains a delocalised π-electron system about the ring. Aryl or arylene groups may comprise from 4-12 atoms, suitably from 6-8 atoms, most suitably 6 atoms. "Aryl" is preferably phenyl (—$C_6H_5$). Arylene is used to define a disubstituted aryl moiety, and is preferably phenylene.

The terms "aryl" or "arylene" in the present invention is also used to include unsaturated heterocycles—rings in which one or more atoms in the ring (e.g. 1-3 atoms) are N, S, P or O. Such heterocycles include pyrrole, furan, thiophene, imidazole, imidazoline, pyrazole, pyrazoline, oxazole, oxazoline, isoxazole, isoxazoline, thiazole, thiazoline, isothiazole, isothiazoline (5-membered rings), pyridine, pyran, thiopyran (6-membered rings).

The term "aryl" also includes fused ring systems and biaryl (particularly biphenyl) systems.

Curing

Curing is primarily initiated by exposing the substances to high energy irradiation, preferably UV light. The photoinitiated process takes place by methods which are known per se, through irradiation with light or UV irradiation in the wavelength range from 100 to 500 nm. Irradiation sources which may be used are sunlight or artificial lamps or lasers. Mercury high-pressure, medium pressure or low-pressure lamps and xenon and tungsten lamps, for example, are advantageous. Similarly, excimer, solid-state and diode-based lasers are advantageous. Diode-based light sources in general are advantageous for initiating the chemical reactions.

The ultraviolet spectrum is divided into A, B and C segments where UV A extend from 400 nm down to 315 nm, UV B from 315 to 280 nm, and UV C from 280 to 100 nm. By using a light source that generates light with wavelengths in the visible region (400 to 800 nm) some advantages are obtained with respect to the depth of the curing, provided that the photoinitiator can successfully cure the material at these wavelengths. In particular, scattering phenomena are less pronounced at longer wavelength, thus giving a larger penetration depth in the material. Thus, photoinitiators which absorb, and can induce curing, at longer wavelength are of interest. By judiciously choosing substituents on the photoinitiator moieties, the absorption spectrum of the photoinitiator can to some extent be red-shifted, which would then facilitate curing at comparatively greater depths.

Photoinitiators and Photoinitiator Moieties

The present invention provides photoinitiators having the general formula (I):

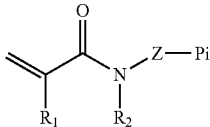
(I)

in which Pi is a photoinitiator moiety;

Z is a linker moiety selected from a single bond, optionally substituted $C_1$-$C_{12}$ alkylene, optionally substituted $C_1$-$C_{12}$ alkenylene; —O—; —S—; —NR$^a$—; —CO—NR$^a$—; optionally substituted heterocyclyl; optionally substituted arylene; optionally substituted —[O—($C_1$-$C_{12}$ alkylene)]$_n$-, optionally substituted —[NHR$^1$—($C_1$-$C_{12}$ alkylene)]$_n$; optionally substituted —[S—($C_1$-$C_{12}$ alkylene)]$_n$-; and combinations thereof; wherein n is an integer from 1-20, and wherein R$^a$ is H or optionally substituted $C_1$-$C_6$ alkyl;

R$^1$ is selected from H or optionally substituted $C_1$-$C_6$ alkyl;

R$^2$ is selected from H or optionally substituted $C_1$-$C_6$ alkyl; wherein R$^2$ or a part thereof may be linked to Z to form one or more ring structures.

A photoinitiator is defined as a substance (other than a reactant) which, on absorption of light, generates reactive species (ions or radicals) and initiates one or several chemical reactions or transformation. One preferred property of the photoinitiator is good overlap between the UV light source spectrum and the photoinitiator absorption spectrum. Another desired property is a minor or no overlap between the photoinitiator absorption spectrum and the intrinsic combined absorption spectrum of the other components in the matrix. Good compatibility of the photoinitiator in the matrix of material to be cured is also a property of interest.

The photoinitiators with the general formula I comprise a photoinitiator moiety, Pi, which provides the photoinitiators with the required response to UV radiation.

The photoinitiator moieties of the invention are efficient in transforming light from the UV or visible light source to reactive radicals which can abstract hydrogen atoms and other labile atoms from other molecules.

Radical photoinitiator moieties can be classified as either cleavable (Norrish type I reaction) or non-cleavable. Upon excitation, Norrish Type-I photoinitiator moieties spontaneously break down into two radicals. In one aspect, the photoinitiator moiety is a Norrish Type-I photoinitiator moiety.

Photoinitiator moieties (Pi) in Formula (I) may be selected from, but not exclusively restricted to, the group consisting: benzoin ethers, 1-phenyl-2-hydroxy-2-alkyl ketones, 1-phenyl-2-amino-2-alkyl ketones, benzophenones, thioxanthones, xanthones, acridones, anthraquinones, fluorenones, dibenzosuberones, benzils, benzil ketals, acetophenones, α-alkoxy-acetophenones, α,α-dialkoxy-acetophenones, α-hydroxy-α-alkyl-phenones, α-hydroxy-α, α-dialkyl-phenones, alkyl phenylglyoxylates, camphorquinones, acyl-phosphine oxides, phenyl ketocoumarins.

Of these, preferred photoinitiator moieties are selected from acetophenones, α-alkoxy-acetophenones, α,α-dialkoxy-acetophenones, α-hydroxy-α-alkyl-phenones, α-hydroxy-α, α-dialkyl-phenones and alkyl phenylglyoxylates.

In particular, Pi may be a Norrish Type-I photoinitiator moiety having the general formula (V):

(V)

wherein Ph is an optionally-substituted phenyl ring;

wherein m is an integer of 1-5, such that m X moieties may be present at any position on Ph;

and wherein X is selected from

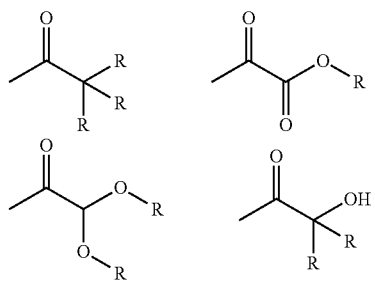

in which R is selected from H or optionally substituted $C_1$-$C_6$ alkyl.

In general formula (V), X is suitably present at the para-position on Ph. Suitably, m is 1 or 2, preferably 1.

Linker, Z

The portion of the photoinitiator of Formula (I) indicated by Z is a linker. Linker Z therefore has two ends. At one end, therefore, Z is joined to the photoinitiator moiety Pi; at the other end, Z is joined to an acrylamide functionality.

The size of the linker Z is selected according to the desired properties of the photoinitiator. Suitably, the linker Z has a molecular weight of less than 10000 Da, suitably less than 5000 Da, most suitably less than 1000 Da. The linker Z preferably comprises no more than 50 atoms, preferably no more than 30 atoms.

In the photoinitiators of Formula (I) above, Z is a linker moiety. Z is be selected from a single bond, optionally substituted $C_1$-$C_{12}$ alkylene, optionally substituted $C_1$-$C_{12}$ alkenylene; —O—; —S—; —NR$^a$—; —CO—NR$^a$—; optionally substituted heterocyclyl; optionally substituted arylene; optionally substituted —[O—($C_1$-$C_{12}$ alkylene)]$_n$-, optionally substituted —[(NHR$^1$—($C_1$-$C_{12}$ alkylene)]$_n$; optionally substituted —[S—($C_1$-$C_{12}$ alkylene)]$_n$-; and combinations thereof; wherein n is an integer from 1-20, and wherein R$^a$ is H or optionally substituted $C_1$-$C_6$ alkyl. The definition of Z excludes ester moieties, which may be susceptible to cleavage under certain conditions.

Suitably, n is an integer from 1-10, more suitably from 1-5, such as e.g. 1, 2, 3, 4 or 5.

In particular embodiments, linker Z may have the structure:

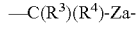

in which the —C(R$^3$)(R$^4$)— moiety is linked to the acrylamide N-atom in formula (I);

wherein Za is a linker moiety selected from a single bond, optionally substituted $C_1$-$C_{12}$ alkylene, optionally substituted $C_1$-$C_{12}$ alkenylene; —O—; —S—; —NR$^a$—; —CO—NR$^a$—; optionally substituted heterocyclyl; optionally substituted arylene; optionally substituted —[O—[($C_1$-$C_{12}$ alkylene)]$_n$-, optionally substituted —(NHR$^1$—($C_1$-$C_{12}$ alkylene)]$_n$; optionally substituted —[S—(C$_1$-C$_{12}$ alkylene)]$_n$-; and combinations thereof; wherein n is an integer from 1-20, and wherein R$^a$ is H or optionally substituted C$_1$-C$_6$ alkyl;

R$^3$ and R$^4$ are independently selected from H or optionally substituted C$_1$-C$_6$ alkyl; wherein R$^3$ or R$^4$, or a part thereof, may be linked to Za to form one or more ring structures. R$^3$ and R$^4$ may independently be selected from optionally substituted C$_1$-C$_6$ alkyl, such as C$_1$-C$_6$ alkyl, e.g. methyl, ethyl or propyl, preferably methyl. In aspects, R$^3$ and R$^4$ are the same.

Photoinitiators with such linkers may be advantageously synthesised via the Ritter reaction. Advantageously, for the Ritter reaction, R$^3$ and R$^4$ are not hydrogen. For the Ritter reaction, R$_2$=H.

In that Z may comprise a combination of the above-mentioned groups, the invention encompasses photoinitiators in which Z is made up of two or more of the above-mentioned groups in series. In all of the above, the —(C$_1$-C$_{12}$ alkylene)- and -aryl-groups may be substituted or unsubstituted. Other chemically-feasible structures for Z can be determined by the person skilled in the art.

Suitably, Z is selected from a single bond, C$_1$-C$_{12}$ alkylene, C$_1$-C$_{12}$ alkenylene; —O—; —S—; —NR$^a$—; or —[O—(C$_1$-C$_{12}$ alkylene)]$_n$-, wherein R$^a$ is H or optionally substituted C$_1$-C$_{12}$ alkyl and n is an integer from 1-20. In aspects, Z is selected from a single bond, C$_1$-C$_{12}$ alkylene or —O—(C$_1$-C$_{12}$ alkylene)-, such as C$_1$-C$_6$ alkylene or —O—(C$_1$-C$_6$ alkylene)-.

Similarly, Za may be selected from a single bond, C$_1$-C$_{12}$ alkylene, C$_1$-C$_{12}$ alkenylene; —O—; —S—; —NR$^a$—; or —[O—(C$_1$-C$_{12}$ alkylene)]$_n$-, wherein R$^a$ is H or optionally substituted C$_1$-C$_{12}$ alkyl and n is an integer from 1-20. In aspects, Za is selected from a single bond, C$_1$-C$_{12}$ alkylene or —O—(C$_1$-C$_{12}$ alkylene)-, such as C$_1$-C$_6$ alkylene or —O—(C$_1$-C$_6$ alkylene)-.

Photoinitiators of Formula (I) in which Z comprises an electron-donating group adjacent to Pi are advantageous, as this provides opportunities to tailor the UV absorption of the photoinitiator moiety.

Other Substituents

In the photoinitiators of general formula (I), R$^1$ is suitably H or methyl. R$^1$ may also be optionally substituted C$_1$-C$_6$ alkyl, such as e.g. methyl, ethyl, propyl, butyl, pentyl or hexyl. R$^1$ may be straight-chain, branched or cyclic alkyl.

R$^2$ is selected from H or optionally substituted C$_1$-C$_6$ alkyl; wherein R$^2$ or a part thereof may be linked to Z to form one or more ring structures. R$^2$ is suitably H.

Further Photoinitiator Structures

A sub-structure which describes photoinitiators of Formula I has the general formula (Ia)

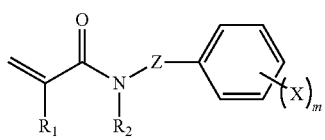

(Ia)

wherein R$^1$, R$^2$, R$^3$, Z, Ph, X, and m are as defined above.

Another sub-structure which describes photoinitiators of Formula (I), has the general formula (Ib):

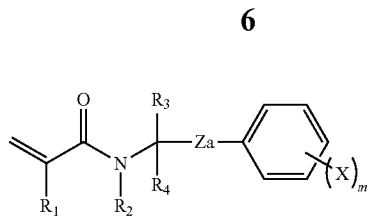

(Ib)

wherein

Za is a linker moiety selected from a single bond, —C$_1$-C$_6$ alkylene- or —O—(C$_1$-C$_6$ alkylene)-;

R$^1$ and R$^2$ are as defined in any one of the preceding claims;

R$^3$ and R$^4$ are independently selected from H or methyl;

X is selected from

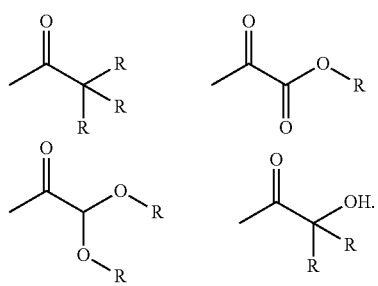

In all sub-structures Ia-Ib, suitable variations of Z, R$^1$ and R$^2$ are as set out above.

Suitable photoinitiators according to the invention include:

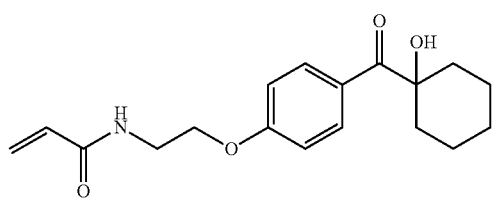

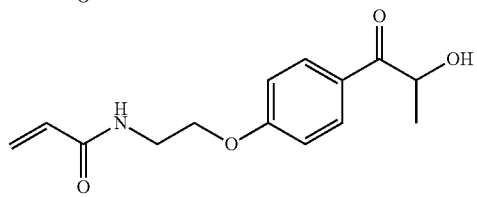

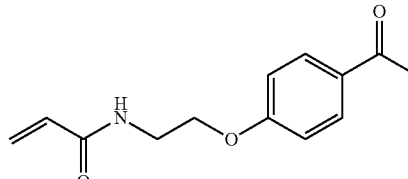

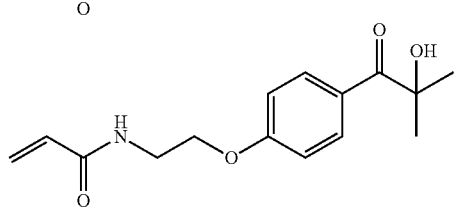

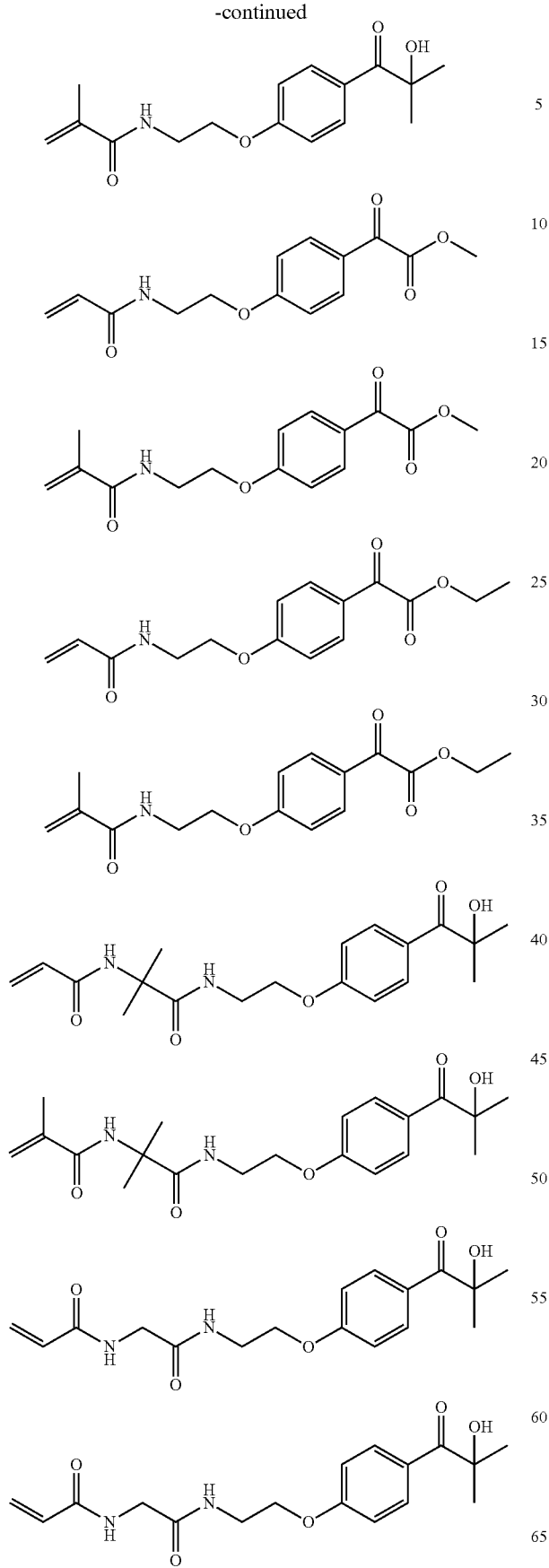

-continued

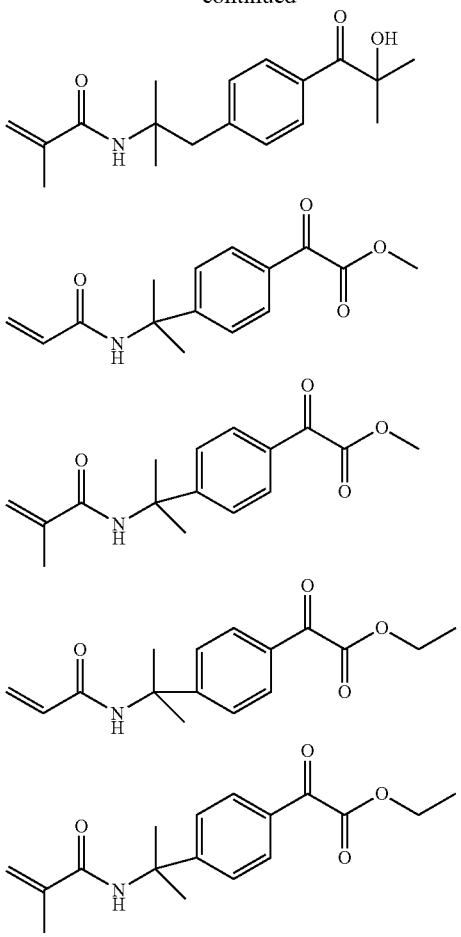

Photoinitiators according to the invention of particular interest are

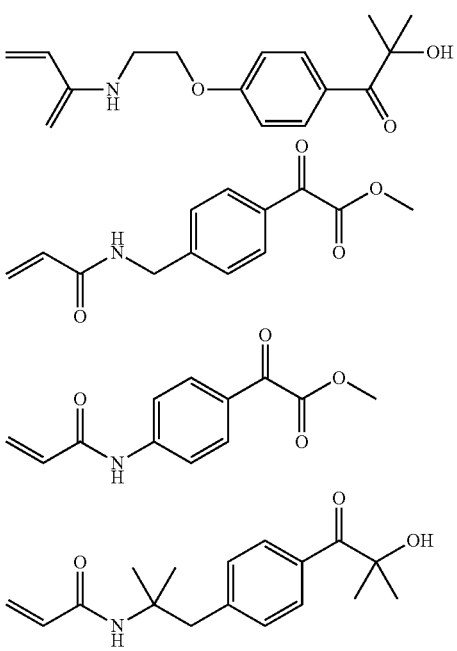

-continued

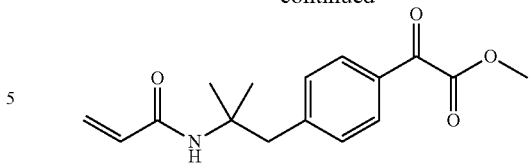

Also provided is a method for synthesising the photoinitiators of the general formula (I), in which $R^2$=H, said method comprising the steps of:

a. reacting an alcohol of the general formula IIa

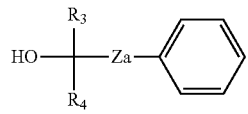

IIa in which Ph, Z, $R^3$ and $R^4$ are as defined herein; with an acrylonitrile of the general formula IIb

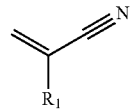

IIb in which $R^1$ is as defined as above;
in a Ritter reaction to form an acrylamide of the general formula IIc:

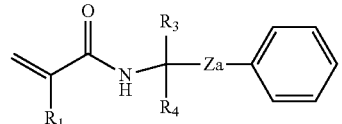

IIc followed by the step of (b) reacting the acrylamide of the general formula IIc in a Friedel-Crafts acylation reaction so as to provide a photoinitiator of the general formula (I).

A route to photoinitiators of the general formula (I). A primary alcohol containing photoinitiator is first activated as an alkyl bromide, then converted to an alkyl azide. The primary amine functionalised photoinitiator is accessed via a Staudinger reduction of the alkyl azide in the presence of a suitable reducing agent. The amine can be conveniently isolated as a hydrochloride salt. Subsequent reaction with a suitable acid chloride in the presence of a base gives the acrylamide or methacrylamide product.

A route to photoinitiators of the general formula (I). A substituted azlactone can be prepared via the cyclisation of an N-acyl-α-amino acid in the presence of a suitable dehydrating agent according to known procedures. Subsequent ring-opening with an amine functionalised photoinitiator gives the acrylamide or methacrylamide product.

A route to photoinitiators of the general formula (I). One way to make precursors to the photoinitiator is by the Ritter reaction. In the reaction, a tertiary alcohol is exposed to strong acids to form a carbocation. This then reacts with a nitrile (acrylonitrile or methacrylonitrile).

Examples of suitable groups as alternatives to tertiary alcohols include benzylic alcohols, geminal disubstituted alkenes and trisubstituted alkenes. Primary and secondary alcohols and mono- and vicinal di-substituted alkenes can sometimes be used, but usually require harsher reaction conditions and give poorer yields. The tertiary carbocations are most stable and common choices for the Ritter reaction are formed from tertiary alcohols or geminal dialkylated alkenes. An aromatic ring adjacent to the carbocation also has a stabilizing effect and benzylic alcohols may thus be used. It is desirable that the carbocation group does not contain anything that strongly activates the aromatic ring to electrophilic attack.

After the Ritter reaction, the ring is acylated to give the final product. Friedel-Crafts acylation with an acid chloride is typically used.

EXAMPLES

Synthesis

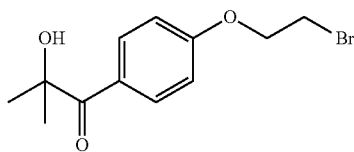

1-[p-(2-Bromoethoxy)phenyl]-2-hydroxy-2-methyl-1-propanone: 33.64 g TPP (0.15 mol) is weighed to a 1 L flask and dissolved in 120 mL dry DCM. >8 mL $Br_2$ is added slowly until a yellow colour persists. A white solid precipitates ($Ph_3PBr_2$). A little TPP is added to get back to colourless. Solution is cooled (ice) and kept under $N_2$. 2.5 mL TEA is added. 2-Hydroxy-1-[4-(2-hydroxyethoxy)phenyl]-2-methylpropan-1-one (33.64 g, 150 mmol) is dissolved in 450 mL DCM+25 mL TEA. This is then added to the cooled suspension over a period of ~1 h from an addition funnel, the ice is removed and the setup is left to heat to RT for 2 h. 5 mL AcOH is added, reaction quenched with water and mix extracted with 3×100 mL brine+(100 mL brine+$NaHCO_3$). Organic phase dried ($Na_2SO_4$), evaporated to dryness. Dried with oil pump/cold trap (~1 mBar). To get rid of most of the TPPO: Redissolved in 250 mL ether. This causes precipitation of crystals (TPPO). Cooled (freezer), filter through a cotton plug, rinse with cold ether, evaporate to dryness. $^1$H NMR (400 MHz, $CDCl_3$); 8.07 (d, J=8.8 Hz, 2H), 6.97 (d, J=8.8 Hz, 2H), 4.36 (t, J=6.2 Hz, 2H), 4.23 (s, 1H), 3.67 (t, J=6.2 Hz, 2H), 1.63 (s, 6H).

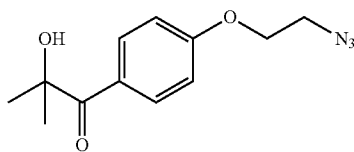 [SMILES: CC(C)(O)C(=O)c1ccc(OCCN=[N+]=[N-])cc1]

1-[p-(2-Azidoethoxy)phenyl]-2-hydroxy-2-methyl-1-propanone: 1-[p-(2-Bromoethoxy)phenyl]-2-hydroxy-2-methyl-1-propanone is dissolved in 450 mL DMF. $NaN_3$ (14.6 g, 225 mmol) is added. The mix is heated to 45° C./stirred until mostly clear solution. Heating turned off after 1 h and the reaction is left overnight at RT. DMF is removed (rotavapor 40° C., end pressure 2 mBar). 200 mL ether is added and mix is filtered, cake rinsed with 100 ml ether. Ether removed. $^1$H NMR (400 MHz, $CDCl_3$); 8.08 (d, J=8.8 Hz, 2H), 6.97 (d, J=8.8 Hz, 2H), 4.24-4.21 (m, 3H), 3.65 (t, J=4.8 Hz, 2H), 1.64 (s, 6H).

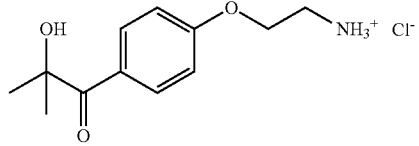 [SMILES: CC(C)(O)C(=O)c1ccc(OCC[NH3+])cc1 ; [Cl-]]

1-[p-(2-Aminoethoxy)phenyl]-2-hydroxy-2-methyl-1-propanone hydrochloride: TPP (47.2 g, 180 mmol) and all of 1-[p-(2-azidoethoxy)phenyl]-2-hydroxy-2-methyl-1-propanone are dissolved in 220 mL MeOH, and refluxed for 1 h. At the start of the reaction, a strong evolution of gas is observed ($N_2$). 20 mL water is added and refluxed for 30 min. Left at RT over weekend. MeOH and water is removed (rotavapor), redissolved in 350 mL ether (precipitation of some of the TPPO). Ether-phase filtered (cotton plug), rinsed with an additional 100 mL ether. Product precipitated with HCl(g). Most of the product precipitates as lumps on the side of the flask. The lumps in the flask are dissolved in 150 mL EtOH to a clear solution. 450 mL ether is added slowly (~1 h) with stirring. The product precipitates as small crystals. The mix is stirred for 30 m, then filtered under $N_2$, rinsed with 2×50 mL ether and dried (vacuum). Yield 22.76 g (54%). $^1$H NMR (400 MHz, $d_6$-DMSO); 8.39 (br s, 3H), 8.18 (d, J=8.7 Hz, 2H), 7.00 (d, J=8.7 Hz, 2H), 5.67 (s, 1H), 4.24 (t, J=4.8 Hz, 2H), 3.17 (t, J=4.8 Hz, 2H), 1.34 (s, 6H).

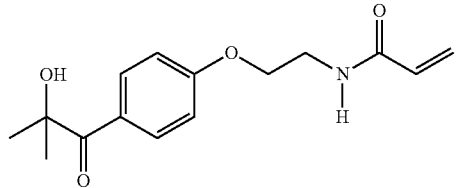 [SMILES: C=CC(=O)NCCOc1ccc(C(=O)C(C)(C)O)cc1]

1-{2-[p-(2-Hydroxy-2-methylpropionyl)phenoxy]ethylamino}-2-propen-1-one: 1-[p-(2-aminoethoxy)phenyl]-2-hydroxy-2-methyl-1-propanone hydrochloride (15.6 g, 60 mmol) is added to a 500 mL 3-neck flask. Flask is mounted with septum and liebig condenser. The flask is heated (heating block 110° C.) and vacuum is applied for 1 h (end pressure 0.09 mBar) to dry starting material, then purged with $N_2$. The flask is cooled to RT and a mix of 100 mg BHT+20 mL dry TEA+300 mL DCM is added with cannula. It is stirred until clear solution. Mix is cooled with $CO_2$(s)/IPA and kept under $N_2$. 4.97 mL acryloyl chloride is added slowly (10 m) with a syringe pump. The setup is left in the cooling bath overnight. Next morning the setup is at RT. The mix is extracted with acidic saturated NaCl, then with aqueous NaCl/$NaHCO_3$. DCM phase dried ($Na_2SO_4$), filtered, evaporated to dryness. It is now an oil—when standing at RT it solidifies to a crystalline mass. 200 mL DIPE is added, refluxed for 10 min. This creates a suspension of crystals in solvent. It is then cooled in ice, pressure filtered and rinsed with 30 mL DIPE. The filtrate is returned to the flask, refluxed for 2 m, cooled and filtered. Product is dried (vacuum). Yield 11.5 g (70%). $^1$H NMR (400 MHz, $CDCl_3$); 7.99 (d, J=9.2 Hz, 2H), 6.86 (d, J=9.2 Hz, 2H), 6.27 (br s, 1H), 6.24 (dd, J=16.8 and 1.2 Hz, 1H), 6.07 (dd, J=16.8 and 10.4 Hz, 1H), 5.60 (dd, J=10.4 and 1.2 Hz, 1H), 4.08 (t, J=5.2 Hz, 2H), 3.72-3.68 (m, 2H), 1.55 (s, 6H).

Synthesis

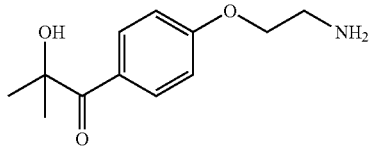 [SMILES: CC(C)(O)C(=O)c1ccc(OCCN)cc1]

1-[4-(2-Aminoethoxy)phenyl]-2-hydroxy-2-methylpropan-1-one: Triphenylphosphine (8.69 g, 33.1 mmol) is added to a solution of 1-[4-(2-azidoethoxy)phenyl]-2-hydroxy-2-methylpropan-1-one (7.50 g, 30.1 mmol) in tetrahydrofuran (120 mL) and water (12 mL) and the solution is stirred at room temperature for 18 h. Water (240 mL) is added and the mixture is acidified to pH 1 using 37% aqueous HCl solution. Impurities are extracted into ethyl acetate (3×100 mL) and the organic washes are discarded. The aqueous phase is basified to pH 14 using 20% aqueous sodium hydroxide solution, then extracted with ethyl acetate (3×150 mL). The combined organic phases are dried (Na$_2$SO$_4$) and concentrated to give the product as a clear liquid (5.70 g, 82%). A $^1$H NMR spectrum of the compound (400 MHz, CDCl$_3$) seems to indicate the formation of a complex mixture of oligomers in solution, nevertheless the product is used in the next step without further purification.

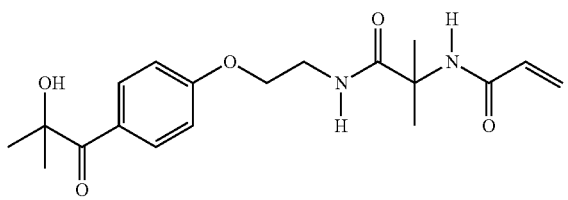 [SMILES: C=CC(=O)NC(C)(C)C(=O)NCCOc1ccc(C(=O)C(C)(C)O)cc1]

N-[1-({2-[4-(2-Hydroxy-2-methylpropanoyl)phenoxy]ethyl}carbamoyl)-1-methylethyl]prop-2-enamide: 1-[4-(2-Aminoethoxy)phenyl]-2-hydroxy-2-methylpropan-1-one (4.70 g, 21.1 mmol) is added to a solution of 4,4-dimethyl-2-vinyloxazol-5(4H)-one (4.90 g, 35.3 mmol) in dichloromethane (150 mL) and the solution is stirred at room temperature for 24 h. The mixture is concentrated under reduced pressure to give the crude product. Column chromatography (eluting with 20:1 dichloromethane-methanol) gives the pure product as a colourless liquid (5.01 g, 70%). $^1$H NMR (400 MHz, d$_6$-Acetone); 8.24 (d, J=8.6 Hz, 2H), 7.56 (br s, 1H), 7.51 (br s, 1H), 6.98 (d, J=8.6 Hz, 2H), 6.28 (dd, J=16.9 and 10.1 Hz, 1H), 6.11 (dd, J=16.9 and 1.8 Hz, 1H), 5.52 (dd, J=10.1 and 1.8 Hz, 1H), 4.74 (s, 1H), 4.13 (t, J=5.9 Hz, 2H), 3.61-3.55 (m, 2H), 1.50 (s, 6H), 1.49 (s, 6H). $^{13}$C NMR (100 MHz, d$_6$-Acetone); 201.88, 174.87, 164.48, 162.67, 133.11, 132.24, 127.92, 125.24, 114.13, 77.36, 66.96, 57.18, 54.67, 39.00, 24.98. ESI-MS m/z 363.2 [MH$^+$].

Synthesis

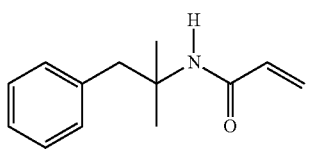

N-(2-Methyl-1-phenylpropan-2-yl)prop-2-enamide: Acrylonitrile (18.0 mL, 0.260 mol) is added to a solution of 2-methyl-1-phenyl-1-propanol (35.0 g, 0.233 mol) in glacial acetic acid (125 mL) at 5-10° C. Concentrated sulfuric acid (13.6 mL, 0.260 mol) is added dropwise while maintaining the reaction temperature at <10° C. The mixture is stirred at room temperature for 16 h, then is heated at 60° C. for 6 h. The mixture is stirred at room temperature for a further 16 h then is cooled in an ice bath to <10° C. Water (300 mL) is added while maintaining the temperature at <20° C., then the resulting slurry is stirred at room temperature for 1 h. The resulting solid is collected by filtration, washed successively with water (3×100 mL) and 40-60° C. petroleum ether (3×100 mL) and is dried thoroughly under vacuum to give the pure product as a colourless solid (44.4 g, 94%). $^1$H NMR (400 MHz, CDCl$_3$); 7.31-7.23 (m, 3H), 7.13-7.11 (m, 2H), 6.25 (dd, J=16.8 and 1.5 Hz, 1H), 5.97 (dd, J=16.8 and 10.3 Hz, 1H), 5.58 (dd, J=10.3 and 1.5 Hz, 1H), 5.16 (br s, 1H), 3.09 (s, 2H), 1.37 (s, 6H).

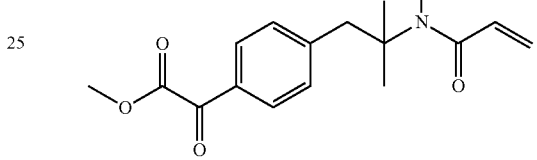

Methyl {4-[2-(acryloylamino)-2-methylpropyl]phenyl}(oxo)acetate: Methyl chlorooxoacetate (16.0 mL, 0.174 mol) is added to a solution of N-(2-methyl-1-phenylpropan-2-yl)prop-2-enamide (25.0 g, 0.123 mol) in dichloromethane (200 mL) at 5-10° C. Aluminium chloride (41.0 g, 0.308 mol) is added portion-wise over 30 minutes and the resulting red solution is stirred at room temperature for 20 h. The resulting heterogeneous slurry is poured into ice water (600 mL) and the mixture is stirred for 15 minutes. Dichloromethane (500 mL) is added and organic materials are extracted into dichloromethane. Combined organic phases are washed with saturated aqueous sodium bicarbonate solution (300 mL), dried (Na$_2$SO$_4$) and concentrated to give the crude product. Recrystallization from tert-butyl methyl ether:hexane gives the pure product as a colourless solid (15.1 g, 42%). $^1$H NMR (400 MHz, CDCl$_3$); 7.91 (d, J=8.3 Hz, 2H), 7.26 (d, J=8.3 Hz, 2H), 6.27 (dd, J=16.8 and 1.5 Hz, 1H), 6.00 (dd, J=16.8 and 10.3 Hz, 1H), 5.62 (dd, J=10.3 and 1.3 Hz, 1H), 5.21 (br s, 1H), 3.97 (s, 3H), 3.24 (s, 2H), 1.37 (s, 6H). $^{13}$C NMR (100 MHz, CDCl$_3$); 186.07, 165.62, 164.69, 146.86, 131.87, 131.63, 130.95, 130.10, 126.90, 54.55, 53.11, 44.48, 27.90.

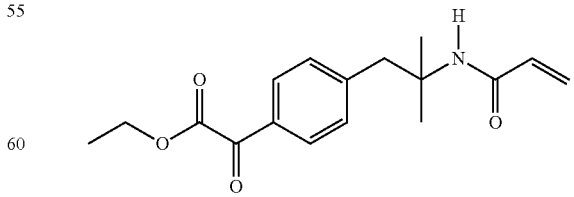

Ethyl {4-[2-(acryloylamino)-2-methylpropyl]phenyl}(oxo)acetate: Ethyl chlorooxoacetate (7.80 mL, 69.7 mmol) is added to a solution of N-(2-methyl-1-phenylpropan-2-yl)prop-2-enamide (10.0 g, 49.8 mmol) in dichloromethane (70 mL) at 5-10° C. Aluminium chloride (16.6 g, 145 mmol) is added portion-wise over 30 minutes and the resulting red solution is stirred at room temperature for 20 h. The heterogeneous slurry is cooled in an ice bath to <10° C. and acetonitrile (20 mL) is added dropwise while maintaining the temperature at <20° C. The resulting homogeneous solution is then poured into ice water (350 mL) and the mixture is stirred for 15 minutes. Dichloromethane (300 mL) is added and organic materials are extracted into dichloromethane. Combined organic phases are washed with saturated aqueous sodium bicarbonate solution (200 mL), dried ($Na_2SO_4$) and concentrated to give the crude product. Recrystallization from tert-butyl methyl ether:hexane gives the pure product as a colourless solid (6.30 g, 42%). $^1$H NMR (400 MHz, $CDCl_3$); 7.90 (d, J=8.2 Hz, 2H), 7.26 (d, J=8.2 Hz, 2H), 6.27 (dd, J=16.8 and 1.4 Hz, 1H), 5.99 (dd, J=16.8 and 10.2 Hz, 1H), 5.62 (dd, J=10.2 and 1.4 Hz, 1H), 5.20 (br s, 1H), 4.43 (q, J=7.2 Hz, 2H), 3.24 (s, 2H), 1.42 (t, J=7.2 Hz, 3H), 1.37 (s, 6H).

Abbreviations used: TPP: triphenyl phosphine, DIPE: diisopropyl ether, DCM: dichloromethane, BHT: butylated hydroxytoluene, IPA: isopropanol, TEA: triethyl amine, DMSO: dimethylsulfoxide, EtOH: ethanol, TPPO: triphenylphosphine oxide, DMF: dimethylformamide, MeOH: methanol, AcOH: acetic acid The photoinitiators are also described in the following numbered aspects:

Aspect 1. A photoinitiator of the formula (I):

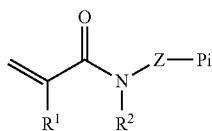

(I)

in which:

Pi is a photoinitiator moiety;

Z is a linker moiety selected from a single bond, optionally substituted $C_1$-$C_{12}$ alkylene, optionally substituted $C_1$-$C_{12}$ alkenylene; —O—; —S—; —$NR^a$—; —CO—$NR^a$—; optionally substituted heterocyclyl; optionally substituted arylene; optionally substituted —[O—($C_1$-$C_{12}$ alkylene)]$_n$-, optionally substituted —[($NHR^1$—($C_1$-$C_{12}$ alkylene)]$_n$-; optionally substituted —[S—($C_1$-$C_{12}$ alkylene)]$_n$-; and combinations thereof; wherein n is an integer from 1-20, and wherein $R^a$ is H or optionally substituted $C_1$-$C_6$ alkyl;

$R^1$ is selected from H or optionally substituted $C_1$-$C_6$ alkyl;

$R^2$ is selected from H or optionally substituted $C_1$-$C_6$ alkyl; wherein $R^2$ or a part thereof may be linked to Z to form one or more ring structures.

Aspect 2. The photoinitiator according to aspect 1, wherein linker Z has the structure:

—C($R^3$)($R^4$)-Zain which the —C($R^3$)($R^4$)— moiety is linked to the acrylamide N-atom in formula (I);

wherein Za is a linker moiety selected from a single bond, optionally substituted $C_1$-$C_{12}$ alkylene, optionally substituted $C_1$-$C_{12}$ alkenylene; —O—; —S—; —$NR^a$—; —CO—$NR^a$—; optionally substituted heterocyclyl; optionally substituted arylene; optionally substituted —[O—($C_1$-$C_{12}$ alkylene)]$_n$-, optionally substituted —[$NHR^1$—($C_1$-$C_{12}$ alkylene)]$_n$-; optionally substituted —[S—($C_1$-$C_{12}$ alkylene)]$_n$-; and combinations thereof; wherein n is an integer from 1-20, and wherein $R^a$ is H or optionally substituted $C_1$-$C_6$ alkyl;

$R^3$ and $R^4$ are independently selected from H or optionally substituted $C_1$-$C_6$ alkyl; wherein $R^3$ or $R^4$, or a part thereof, may be linked to Za to form one or more ring structures.

Aspect 3. The photoinitiator according to aspect 2, wherein $R^3$ and $R^4$ are independently selected optionally substituted $C_1$-$C_6$ alkyl, such as $C_1$-$C_6$ alkyl, e.g. methyl, ethyl or propyl, preferably methyl.

Aspect 4. The photoinitiator according to any one of aspects 2-3, wherein $R^3$ and $R^4$ are the same.

Aspect 5. The photoinitiator according to any one of the preceding aspects, wherein Z is selected from a single bond, $C_1$-$C_{12}$ alkylene, $C_1$-$C_{12}$ alkenylene; —O—; —S—; —$NR^a$—; or —[O—($C_1$-$C_{12}$ alkylene)]$_n$-, wherein $R^a$ is H or optionally substituted $C_1$-$C_{12}$ alkyl and n is an integer from 1-20.

Aspect 6. The photoinitiator according to any one of the preceding aspects, wherein Z is selected from a single bond, $C_1$-$C_{12}$ alkylene or —O—($C_1$-$C_{12}$ alkylene)-, such as $C_1$-$C_6$ alkylene or —O—($C_1$-$C_6$ alkylene)-.

Aspect 7. The photoinitiator according to any one of aspects 2-4, wherein Za is selected from a single bond, $C_1$-$C_{12}$ alkylene, $C_1$-$C_{12}$ alkenylene; —O—; —S—; —$NR^a$—; or —[O—($C_1$-$C_{12}$ alkylene)]$_n$-, wherein $R^a$ is H or optionally substituted $C_1$-$C_{12}$ alkyl and n is an integer from 1-20.

Aspect 8. The photoinitiator according to aspect 7, wherein Za is selected from a single bond, $C_1$-$C_{12}$ alkylene or —O—($C_1$-$C_{12}$ alkylene)-, such as $C_1$-$C_6$ alkylene or —O—($C_1$-$C_6$ alkylene)-.

Aspect 9. The photoinitiator according to any one of the preceding aspects, in which $R^1$ is H or methyl, preferably H.

Aspect 10. The photoinitiator according to any one of the preceding aspects, wherein Pi is a Norrish type-I photoinitiator moiety.

Aspect 11. The photoinitiator according to any one of the preceding aspects, wherein Pi is selected from the group consisting of: benzoin ethers, 1-phenyl-2-hydroxy-2-alkyl ketones, 1-phenyl-2-amino-2-alkyl ketones, dibenzosuberones, benzils, benzil ketals, acetophenones, α-alkoxy-acetophenones, α,α-dialkoxy-acetophenones, α-hydroxy-α-alkyl-phenones, α-hydroxy-α, α-dialkyl-phenones, alkyl phenylglyoxylates, camphorquinones, acyl-phosphine oxides, phenyl ketocoumarins.

Aspect 12. The photoinitiator according to any one of the preceding aspects, wherein Pi is a photoinitiator moiety selected from the group consisting of: acetophenones, α-alkoxy-acetophenones, α,α-dialkoxy-acetophenones, α-hydroxy-α-alkyl-phenones, α-hydroxy-α, α-dialkyl-phenones and alkyl phenylglyoxylates.

Aspect 13. A photoinitiator according to any one of the preceding aspects, wherein Pi is a Norrish Type-I photoinitiator moiety having the general formula (V):

-Ph-(X)$_m$ (V)

wherein Ph is an optionally-substituted phenyl ring;

wherein m is an integer of 1-5, such that m X moieties may be present at any position on Ph;

and wherein X is selected from

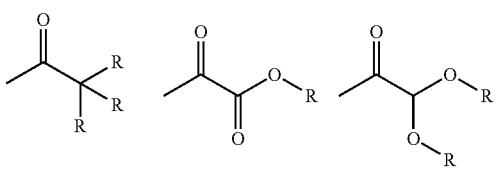

-continued

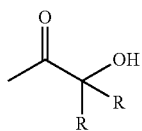

in which R is selected from H or optionally substituted $C_1$-$C_6$ alkyl.

Aspect 14. The photoinitiator according to aspect 13, wherein said X is present at the para-position on Ph.

Aspect 15. The photoinitiator according to any one of aspects 13-14, wherein m is 1 or 2, preferably 1.

Aspect 16. The photoinitiator according to any one of aspects 1-15, having the general formula (Ia):

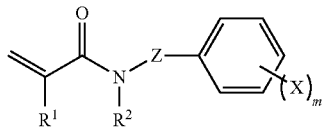

(Ia)

wherein $R^1$, $R^2$, $R^3$, Z, X, and m are as defined in any one of aspects 1-15.

Aspect 17. The photoinitiator according to any one of aspects 1-16, having the general formula (Ib):

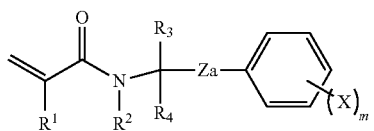

(Ib)

wherein

Za is a linker moiety selected from a single bond, —$C_1$-$C_6$ alkylene- or —O—($C_1$-$C_6$ alkylene)-;

$R^1$ and $R^2$ are as defined in any one of the preceding aspects;

$R^3$ and $R^4$ are independently selected from H or methyl;

X is selected from

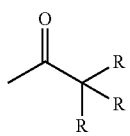 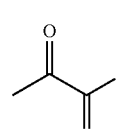 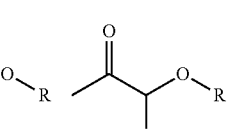

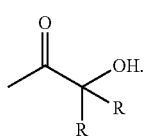

Aspect 18. A photoinitiator according to any one of aspects 1-17, being selected from:

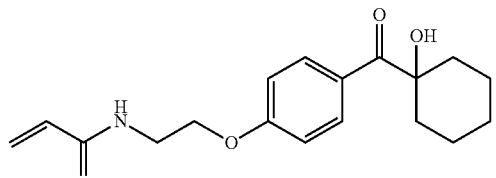

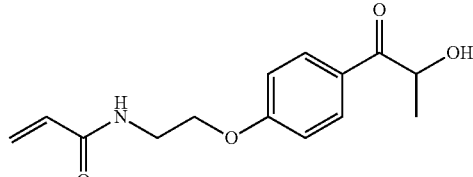

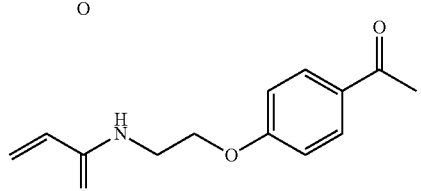

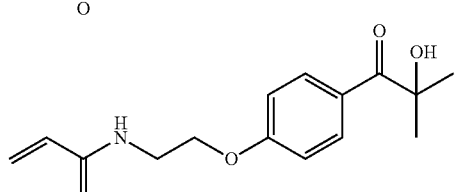

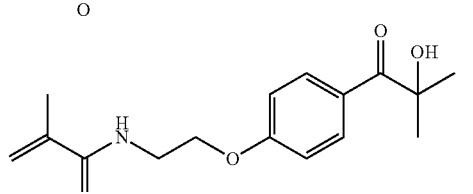

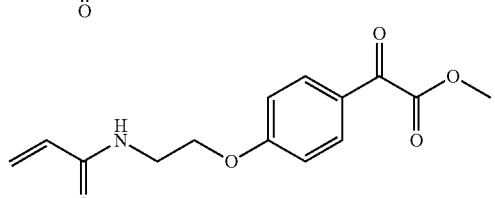

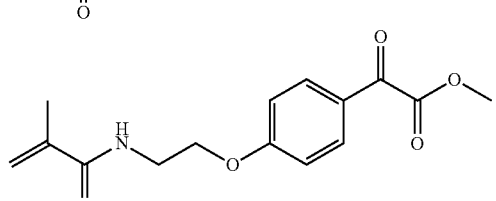

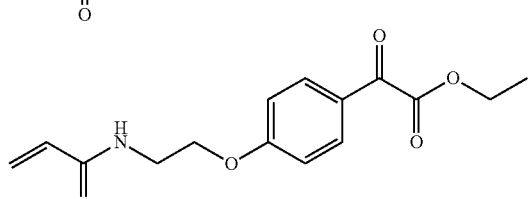

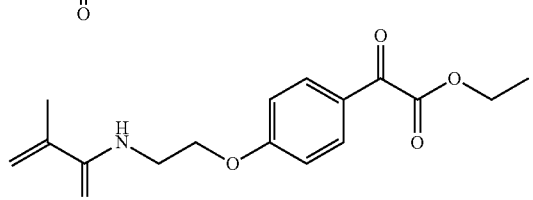

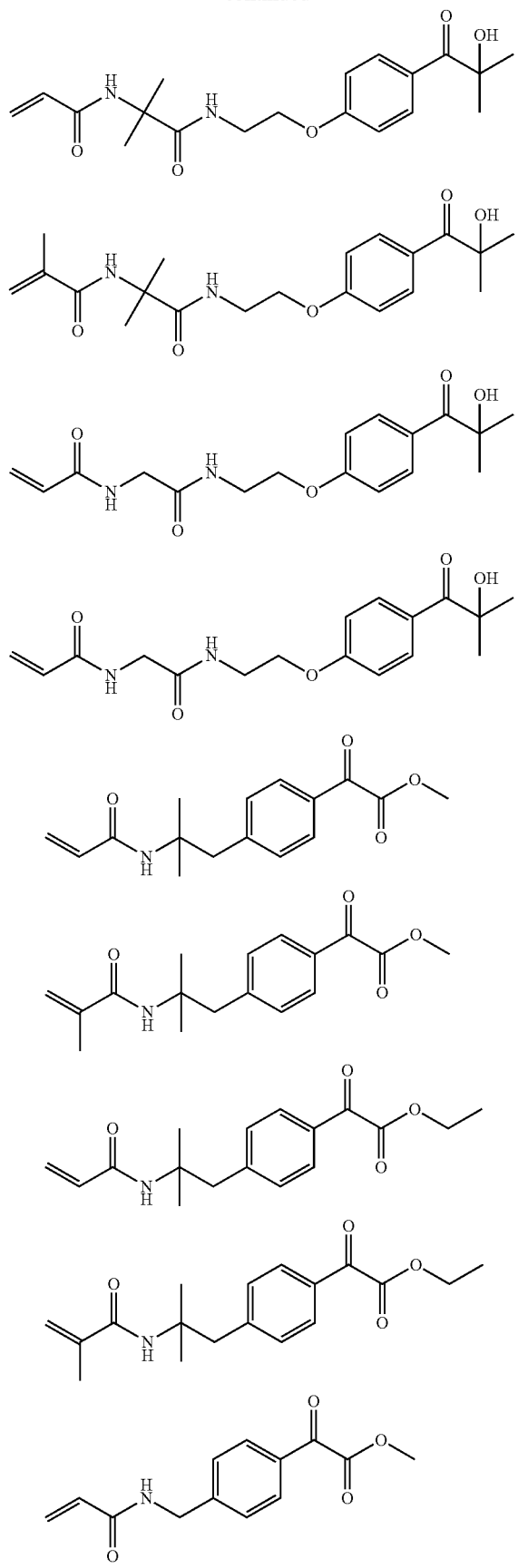
Aspect 19. A method for synthesising the photoinitiators of the general formula (I), in which R²=H, said method comprising the steps of:

The invention claimed is:

1. A method for synthesizing the photoinitiators of the formula (I)

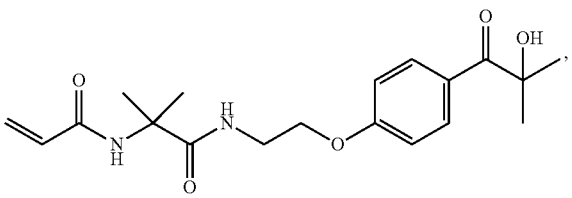 [SMILES: C=CC(=O)NC(C)(C)C(=O)NCCOc1ccc(C(=O)C(C)(C)O)cc1]

comprising the step of reacting

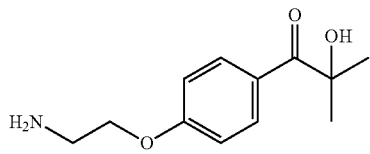 [SMILES: CC(C)(O)C(=O)c1ccc(OCCN)cc1]

with

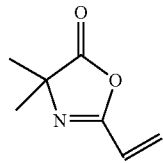

to provide the photoinitiators of the formula (I).

a. reacting an alcohol of the general formula IIa

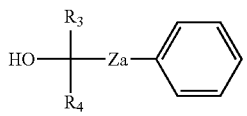
IIa in which Za, $R^3$ and $R^4$ are as defined in any one of aspects 1-18; with an acrylonitrile of the general formula IIb

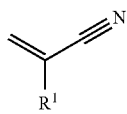
IIb in which $R^1$ is as defined in any one of aspects 1-17;
in a Ritter reaction to form an acrylamide of the general formula IIc:

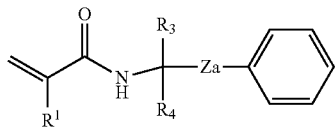
IIc followed by the step of (b) reacting the acrylamide of the general formula IIc in a Friedel-Crafts acylation reaction so as to provide a photoinitiator of the general formula (I).

Although the invention has been described with reference to a number of examples and reaction schemes, it should not be considered as limited by the above description. The full scope of the invention is defined by the appended claims.

\* \* \* \* \*